(12) United States Patent
Furno et al.

(10) Patent No.: US 8,071,202 B2
(45) Date of Patent: Dec. 6, 2011

(54) WATER-ABSORBING POLYMER STRUCTURES WITH IMPROVED ABSORPTION PROPERTIES

(75) Inventors: Franck Furno, Düsseldorf (DE); Harald Schmidt, Tonisvorst (DE); Peter Herbe, Dulsburg (DE); Ursula Nielinger, Krefeld (DE); Michael Keup, Essen (DE)

(73) Assignee: Evonik Stockhausen GmbH, Krefeld (DE)

( * ) Notice: Subject to any disclaimer, the term of this patent is extended or adjusted under 35 U.S.C. 154(b) by 911 days.

(21) Appl. No.: 11/912,011

(22) PCT Filed: Apr. 21, 2006

(86) PCT No.: PCT/EP2006/003694
§ 371 (c)(1),
(2), (4) Date: Mar. 18, 2008

(87) PCT Pub. No.: WO2006/111402
PCT Pub. Date: Oct. 26, 2006

(65) Prior Publication Data
US 2009/0202805 A1    Aug. 13, 2009

(30) Foreign Application Priority Data
Apr. 22, 2005  (DE) .......................... 10 2005 018 924

(51) Int. Cl.
*B32B 7/02* (2006.01)

(52) U.S. Cl. ......... 428/212; 428/219; 428/220; 525/474
(58) Field of Classification Search .................. 428/212, 428/219, 220; 525/474
See application file for complete search history.

(56) References Cited

U.S. PATENT DOCUMENTS

| | | | |
|---|---|---|---|
| 4,076,663 A | 2/1978 | Masuda et al. | |
| 4,131,576 A | 12/1978 | Iovine et al. | |
| 4,179,367 A | 12/1979 | Barthell et al. | |
| 4,286,082 A | 8/1981 | Tsubakimoto et al. | |
| 4,340,706 A | 7/1982 | Obayashi et al. | |
| 4,587,308 A | 5/1986 | Makita et al. | |
| 5,409,771 A | 4/1995 | Dahmen et al. | |
| 5,562,646 A | 10/1996 | Goldman et al. | |
| 5,599,335 A | 2/1997 | Goldman et al. | |
| 5,610,220 A | 3/1997 | Klimmek et al. | |
| 5,669,894 A | 9/1997 | Goldman et al. | |
| 5,672,633 A | 9/1997 | Brehm et al. | |
| 5,684,106 A | 11/1997 | Johnson et al. | |
| 5,712,316 A | 1/1998 | Dahmen et al. | |
| 5,760,080 A | 6/1998 | Wada et al. | |
| 5,973,042 A | 10/1999 | Yoshinaga | |
| 6,060,557 A | 5/2000 | Dahmen et al. | |
| 6,087,450 A * | 7/2000 | Breitbach et al. ............. | 525/242 |
| 6,300,275 B1 | 10/2001 | Weir | |
| 6,403,700 B1 | 6/2002 | Dahmen et al. | |
| 6,605,673 B1 | 8/2003 | Mertens et al. | |
| 6,620,889 B1 | 9/2003 | Mertens et al. | |
| 7,157,141 B2 | 1/2007 | Inger et al. | |
| 7,179,862 B2 | 2/2007 | Mertens et al. | |
| 2003/0040570 A1 | 2/2003 | Nestler et al. | |
| 2003/0125684 A1 | 7/2003 | Qin | |
| 2004/0220350 A1* | 11/2004 | Smith et al. ................. | 525/328.2 |
| 2005/0020780 A1 | 1/2005 | Inger et al. | |
| 2006/0029782 A1 | 2/2006 | Harren et al. | |
| 2006/0057389 A1 | 3/2006 | Reimann et al. | |
| 2007/0066754 A1 | 3/2007 | Loeker et al. | |
| 2007/0129495 A1 | 6/2007 | Mertens et al. | |
| 2008/0221277 A1 | 9/2008 | Furno et al. | |
| 2008/0280128 A1 | 11/2008 | Furno et al. | |

FOREIGN PATENT DOCUMENTS

| | | |
|---|---|---|
| CA | 2352579 | 6/2000 |
| DE | 2706135 | 8/1978 |
| DE | 2840010 | 6/1979 |
| DE | 3503458 A1 | 8/1985 |
| DE | 3713601 A1 | 11/1988 |
| DE | 4020780 C1 | 8/1991 |
| DE | 4244548 A1 | 7/1994 |
| DE | 4418818 A1 | 1/1995 |
| DE | 4333056 A1 | 3/1995 |
| DE | 19529348 A1 | 2/1997 |
| DE | 19854575 A1 | 5/2000 |
| DE | 19909653 A1 | 9/2000 |
| DE | 19909838 A1 | 9/2000 |
| DE | 10016041 A1 | 10/2001 |
| DE | 10138630 A1 | 2/2003 |
| DE | 10249821 A1 | 5/2004 |
| DE | 10249822 A1 | 5/2004 |
| DE | 10334286 A1 | 3/2005 |
| EP | 0640330 A1 | 3/1995 |

(Continued)

OTHER PUBLICATIONS

English Translation of International Preliminary Report on Patentability mailed on Apr. 24, 2008 in PCT/EP2006/003694.
Mirko Walden et al., U.S. Appl. No. 12/297,480, filed with U.S. Patent and Trademark Office on Oct. 17, 2008.

*Primary Examiner* — David Sample
*Assistant Examiner* — Lawrence Ferguson
(74) *Attorney, Agent, or Firm* — Smith Moore Leatherwood LLP; Philip P. McCann

(57) ABSTRACT

The present invention relates to a process for production of water-absorbing polymer structures comprising the process steps of providing an untreated, water-absorbing polymer structure (Pu) with a retention of at least about 35 g/g; and bringing this water-absorbing untreated polymer structure (Pu) into contact with a permeability-increasing agent. The invention further relates to the water-absorbing polymer structures obtainable by this process, water-absorbing polymer structures, a composite, a process for production of a composite, a composite obtainable by this process, chemical products comprising water-absorbing polymer structures or a composite as well as the use of water-absorbing polymer structures or of the composite in chemical products.

16 Claims, 1 Drawing Sheet

FOREIGN PATENT DOCUMENTS

Figure 1:
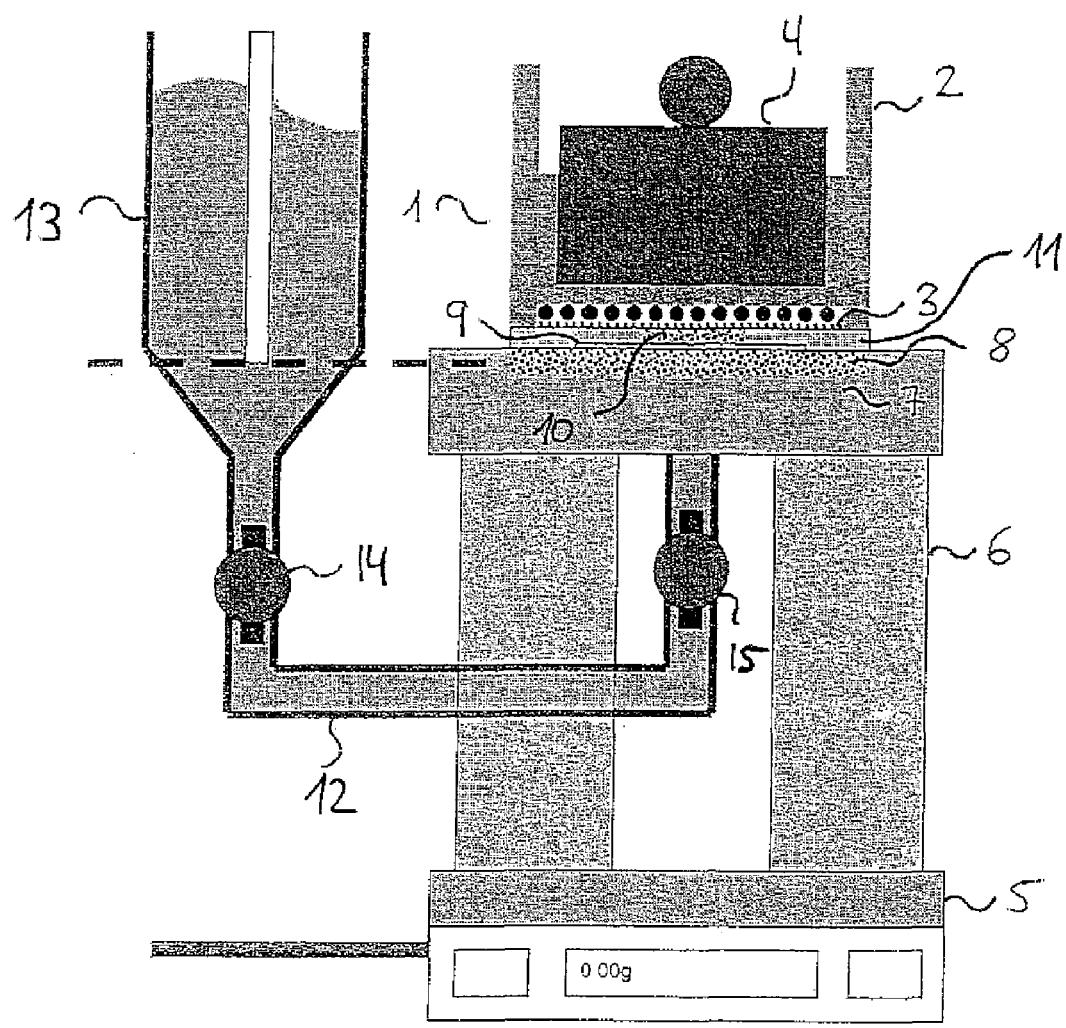

| | | |
|---|---|---|
| EP | 0951913 A1 | 10/1999 |
| EP | 1358892 A1 | 11/2003 |
| WO | 9522356 A | 8/1995 |
| WO | 9848857 A | 11/1998 |
| WO | 9849221 A | 11/1998 |
| WO | 9934843 | 7/1999 |
| WO | 9955767 | 11/1999 |
| WO | 0053644 | 9/2000 |
| WO | 0053664 | 9/2000 |
| WO | 0174913 A1 | 10/2001 |
| WO | 2004037900 A1 | 5/2004 |
| WO | 2004037903 A2 | 5/2004 |
| WO | 2006094907 A1 | 9/2006 |
| WO | 2006111403 A1 | 10/2006 |
| WO | 2006111404 A2 | 10/2006 |
| WO | 2007121941 A2 | 11/2007 |

* cited by examiner

WATER-ABSORBING POLYMER STRUCTURES WITH IMPROVED ABSORPTION PROPERTIES

This application is a national stage application under 35 U.S.C. 371 of international application No. PCT/EP2006/003694 filed 21 Apr. 2006, and claims priority to German Application No. DE 10 2005 018 924.5 filed 22 Apr. 2005, the disclosure of which is expressly incorporated herein by reference.

BACKGROUND

The present invention relates to a process for production of water-absorbing polymer structures, the water-absorbing polymer structures obtainable by this process, water-absorbing polymer structures, a composite, a process for production of a composite, a composite obtainable by this process, chemical products comprising water-absorbing polymer structures or a composite, as well as the use of water-absorbing polymer structures or of the composite in chemical products.

Superabsorbers are water-insoluble, crosslinked polymers, which are capable of absorbing, and retaining under a given pressure, large quantities of aqueous liquids, in particular body fluids, preferably urine or blood, by swelling and forming hydrogels. Because of these characteristic properties, these polymers principally find applications by incorporation into sanitary articles, such as, for example, baby diapers, incontinence products, or sanitary napkins.

Superabsorbers which are presently commercially available are mostly crosslinked polyacrylic acids or crosslinked starch acrylic acid graft polymers, in which the carboxyl groups are partially neutralized with sodium hydroxide or potassium hydroxide.

For aesthetic and environmental reasons, there is an increasing tendency to make sanitary articles ever smaller and thinner. In order to guarantee a consistent overall retention capacity of the sanitary article, this demand can only be accommodated by reduction of the proportion of voluminous fluff. This means that further tasks fall to the superabsorber in respect of transport and distribution of liquids, which can be summarized as permeability properties.

By permeability in superabsorber materials is understood the capacity, in the swollen state, to transport and uniformly distribute penetrating liquids within the swollen gel. This process occurs via capillary transport through spaces between the gel particles. Liquid transport through the swollen superabsorber particles itself follows the laws of diffusion and is a very slow process which plays no role in the distribution of liquid in the use situation of the sanitary article. For superabsorber materials which cannot accomplish a capillary transport because of lacking gel stability, a separation of the particles from each other, with avoidance of the gel blocking phenomenon, is effected by the embedding of these materials into a fiber matrix. In diaper constructions of newer generations, there is only little or even no fiber material in the absorber layer to support liquid transport. The superabsorbers used here must correspondingly have a sufficiently high stability in the swollen state for the swollen gel to have a sufficient amount of capillary spaces, through which liquid can be transported.

In order to obtain superabsorber materials with high gel stability, on the one hand, the degree of crosslinking of the polymer can be increased, which necessarily results in a reduction of the swell capability and of the retention capacity.

Furthermore, methods for post-treating of the surface of polymer particles for improvement of the superabsorber properties can be used. Surface treatments known from the state of the art are, for example, the post-crosslinking of the water-absorbing polymer structure at the surface, the bringing into contact of the surface with inorganic compounds, or the post-crosslinking of the surface in the presence of inorganic compounds.

DE-A-100 16 041 achieves a restoration of the gel permeability of water-absorbing polymers, which has been damaged by mechanical action, by post-treating such a polymer after a post-crosslinking with a solution of at least one salt of an at least trivalent cation.

WO-A-98/48857 discloses superabsorbent polymers having an improved Gel Bed Resiliency, which was obtained by the dry mixing of the polymers with a multivalent metal salt and the subsequent contacting of the mixture with a binding agent. A mixing of this type with inorganic, fine particulate substances has disadvantages, such as, for example, demixing or dust.

WO-A-98/49221 describes the rewetting of water-absorbing polymers with an aqueous solution of an additive comprising a mono- or multivalent metal salt after a heat treatment, which leads to polymers with improved processability.

The disadvantage of the water-absorbing polymer structures known from the state of the art is, however, among others, that absorbent structures, such as, for example, absorbent cores in diapers, comprise as absorption agents previous polymer structures with higher absorption capacity, which, upon sudden entry of particularly large amounts of body fluids, as can occur, for example, with adult diaper wearers or upon wetting of a diaper by an older child suffering from *Enuresis nocturna* ("bed-wetting"), are not capable of fully absorbing and further distributing within the absorbent structure the amount of fluid, in particular under a pressure caused by the lying diaper wearer.

In general, the invention has the object of overcoming the disadvantages arising from the state of the art.

SUMMARY

In particular, the present invention had the object of providing water-absorbing polymer structures with high absorption capacity, which, in comparison to previous absorption agents, enable an improved liquid absorption and further distribution upon use in absorbent structures, such as, for example, diapers. In particular, the water-absorbing polymer structures with high absorption capacity should also be capable of ensuring a rapid absorption and uniform further distribution of suddenly entering, particularly large amounts of body fluids under a load, when used in diapers for adults or for diaper wearers suffering from *Enuresis nocturna*.

An additional object according to the invention is to provide a process with which such water-absorbing polymer structures can be made in a simple, as far as possible continuous way and with the smallest possible amounts of organic solvent. In this production process, added powdery additives should detach at most in small amounts from the polymer structures and should not negatively influence the polymer properties.

FIGURES

The foregoing and other features, aspects, and advantages of the present invention will become better understood with regard to the following description, appended claims, and accompanying drawing where:

FIG. 1 shows the device for determination of the TAAP value by means of the test process described herein.

DETAILED DESCRIPTION

A contribution to the solution of the above-mentioned objects is provided by a process for production of water-absorbing polymer structures comprising the process steps:
I. providing an untreated, water-absorbing polymer structure (Pu) with a retention determined according to the test method described herein of at least about 37.5 g/g, or at least about 38 g/g, or at least about 39 g/g, or at least about 41 g/g, or at least about 43 g/g, whereby a retention value of about 75 g/g, or about 70 g/g, or about 65 g/g, or about 60 g/g, or about 55 g/g is not exceeded;
II. bringing into contact of this untreated water-absorbing polymer structure (Pu) with a permeability-increasing agent, whereby the permeability-increasing agent may be a SiO compound, a salt comprising a multivalent, or trivalent cation, or a mixture of a SiO compound and a salt comprising a multivalent, such as a trivalent cation.

An "untreated, water-absorbing polymer structure (Pu)" is defined as a polymer structure which has not yet been brought into contact with a permeability-increasing agent, such as not yet with a SiO compound, with a salt comprising a multivalent, such as a trivalent cation, or with a mixture of a SiO compound and a salt comprising a multivalent, such as a trivalent cation. This does not, however, exclude that the water-absorbing polymer structure has been modified, for example in another way, for example by means of a surface post-crosslinking.

In one aspect of the process according to the invention, it is preferred that the retention of the untreated water-absorbing polymer structure lies within a range from about 37.1 to about 60 g/g, or from about 37.1 to about 55 g/g, or from about 37.1 to about 50 g/g, or from about 40 to about 50 g/g.

Completely surprisingly, but nonetheless advantageous, it was found that the surface treatment of precursor particles with a high retention of at least about 37.5 g/g, which are generally characterized by a negligible permeability, water-absorbing polymer structures may be obtained, which show a very good liquid absorption and liquid distribution behavior in absorbent structures with high amounts of superabsorber.

Water-absorbing polymer structures preferred according to the invention are fibers, foams, or particles, whereby fibers and particles are preferred and particles are particularly preferred. Water-absorbing polymer structures in these forms are obtained by using correspondingly fibers, foams, or particles as untreated, water-absorbing polymer structures (Pu).

Polymer fibers according to the invention are so dimensioned that they can be incorporated in or as yarns for textiles and also directly in textiles. In an embodiment of this invention, the polymer fibers have a length within the range from 1 to about 500 mm, or from about 2 to about 500 mm, or from about 5 to about 100 mm, and a diameter within the range from about 1 to about 200 Denier, or from about 3 to about 100 Denier, or from about 5 to about 60 Denier.

Water-absorbing polymer particles according to the invention may be dimensioned such that they have an average particle size according to ERT 420.2-02 within the range from about 10 to about 3,000 µm, or from about 20 to about 2,000 µm, or from about 150 to about 850 µm, or from about 150 to about 600 µm. The water-absorbing polymer particles according to the present invention may include to at least about 30 wt. %, or to at least about 40 wt. %, or to at least about 50 wt. % on particles with a particle size within a range from about 300 to about 600 µm.

The untreated water-absorbing polymer structure (Pu) provided in process step I of the inventive process is preferably a polymer structure which is based upon ($\alpha$1) from about 20 wt % to about 99.999 wt %, or from about 55 to about 98.99 wt %, or from about 70 wt % to about 98.79 wt % of polymerized, ethylenically unsaturated, acid groups-carrying monomers or salts thereof or polymerized, ethylenically unsaturated monomers comprising a protonated or quaternated nitrogen, or mixtures thereof, whereby mixtures comprising at least ethylenically unsaturated, acid groups-comprising monomers, or acrylic acid, ($\alpha$2) from 0 to about 80 wt %, or from 0 to about 44.99 wt %, or from 0.1 to about 44.89 wt % of polymerized, monoethylenically unsaturated monomers which are co-polymerizable with ($\alpha$1), ($\alpha$3) from 0.001 to about 5 wt %, or from 0.01 to about 3 wt %, or from 0.01 to about 0.5 wt % of one or more crosslinkers, ($\alpha$4) from 0 to about 30 wt %, or from 0 to about 5 wt %, or from 0.1 wt % to about 5 wt % of a water-soluble polymer, ($\alpha$5) from 0 to about 20 wt %, or from about 2.5 wt % to about 15 wt %, or from 3 wt % to about 6 wt % water, and ($\alpha$6) from 0 to about 20 wt %, or from 0 to about 10 wt %, or from 0.1 to about 8 wt % of one or more additives, whereby the sum of the weight amounts ($\alpha$1) to ($\alpha$6) is 100 wt. %.

The monoethylenically unsaturated, acid groups-comprising monomers ($\alpha$1) may be partially or fully neutralized. The monoethylenically unsaturated, acid groups-comprising monomers may be neutralized to at least about 25 mol %, or to at least about 50 mol %, or from about 50 to about 80 mol %. In this context, reference is made to DE 195 29 348 A1. The neutralization can also occur partially or fully after the polymerization. Furthermore, the neutralization may be carried out with alkali metal hydroxides, alkaline earth metal hydroxides, and ammonia, as well as carbonates and bicarbonates. In addition, any further base which forms a water-soluble salt with the acid is conceivable. A mixed neutralization with different bases is also conceivable. Neutralization with ammonia and alkali metal hydroxides is preferred, particularly preferred with sodium hydroxide and with ammonia.

Furthermore, the free acid groups may predominate in a polymer, so that this polymer may have a pH value lying in the acidic range. This acidic water-absorbing polymer may be at least partially neutralized by a polymer with free basic groups, or amine groups, which is basic compared to the acidic polymer. These polymers are described in the literature as "Mixed-Bed Ion-Exchange Absorbent Polymers" (MBIEA-Polymers) and are disclosed in WO 99/34843. MBIEA polymers may have a composition that comprises on the one hand basic polymers, which are able to exchange anions, and on the other hand, a polymer which is acidic in comparison to the basic polymer, which is capable of exchanging cations. The basic polymer comprises basic groups and is typically obtained by polymerization of monomers which carry basic groups, or groups which can be converted into basic groups. These monomers may comprise primary, secondary, or tertiary amines or corresponding phosphines, or at least two of the above functional groups. In particular ethyleneamine, allylamine, diallylamine, 4-aminobutene, alkyloxycycline, vinylformamide, 5-aminopentene, carbodiimide, formaldacine, melamine, and the like, as well as their secondary or tertiary amine derivatives, belong to this group of monomers.

As ethylenically unsaturated, acid groups-comprising monomers ($\alpha$1), those compounds are used which are mentioned as ethylenically unsaturated acid groups-comprising monomers ($\alpha$1) in WO-A-2004/037903, which is hereby limitedly incorporated as reference only as to the disclosure of ethylenically unsaturated acid groups-comprising monomers. Ethylenically unsaturated, acid groups-comprising monomers ($\alpha 1$) may include acrylic acid and methacrylic acid.

According to an embodiment of the process according to the invention, water-absorbing polymer structures are used, in which the monoethylenically unsaturated monomers ($\alpha 2$) which may be co-polymerizable with ($\alpha 1$) are acrylamides, methacrylamides or vinylamides.

(Meth)acrylamides may include, besides acrylamide and methacrylamide, alkyl-substituted (meth)acrylamides or aminoalkyl-substituted derivatives of (meth)acrylamide, such as N-methylol(meth)acrylamide, N,N-dimethylamino (meth)acrylamide, dimethyl(meth)acrylamide or diethyl (meth)acrylamide. Possible vinyl amides are, for example, N-vinylamides, N-vinylformamides, N-vinylacetamides, N-vinyl-N-methylacetamide, N-vinyl-N-methylformamides, and vinylpyrrolidone.

According to another embodiment of the process according to the invention, as untreated water-absorbing polymer structures (Pu), polymer structures are used, in which the monoethylenically unsaturated monomers ($\alpha 2$) which are co-polymerizable with ($\alpha 1$) may be water-soluble monomers. In this context, alkoxypolyalkyleneoxide(meth)acrylates such as methoxypolyethylene glycol(meth)acrylates may be used.

Further preferred as monoethylenically unsaturated monomers ($\alpha 2$) which are co-polymerizable with ($\alpha 1$) are water-dispersible monomers. Water-dispersible monomers may include acrylic acid esters and methacrylic acid esters, such as methyl(meth)acrylate, ethyl(meth)acrylate, propyl(meth) acrylate or butyl(meth)acrylate.

The monoethylenically unsaturated monomers ($\alpha 2$) which are co-polymerizable with ($\alpha 1$) may further comprise methylpolyethylene glycol allylethers, vinylacetate, styrene, and isobutylene.

Crosslinker ($\alpha 3$) is mentioned in WO-A-2004/037903 including water-soluble crosslinkers. Examples of crosslinker ($\alpha 3$) may include N,N'-methylenebisacrylamide, polyethylene glycol di(meth)acrylates, triallylmethylammonium chloride, tetraallylammonium chloride, as well as allylnonaethylene glycol acrylate prepared with 9 mol ethylene oxide per mol of acrylic acid.

As water-soluble polymers ($\alpha 4$), water-soluble polymers, such as partially or fully saponified polyvinyl alcohol, polyvinyl pyrrolidone, starches or starch derivatives, polyglycols, or polyacrylic acids may be comprised in the water-absorbing untreated polymer structures (Pu). The molecular weight of these polymers may not be critical, as long as they are water-soluble. Water-soluble polymers may include starches or starch derivatives, or polyvinyl alcohol. The water-soluble polymers, preferably synthetic such as polyvinyl alcohol, can also serve as a graft basis for the monomers to be polymerized.

As additive ($\alpha 6$), preferably suspending agents, odor binders, surfactants, or anti-oxidants may be comprised in the water-absorbing, untreated polymer structures (Pu). Furthermore, comprised in the water-absorbing, untreated polymer structures (Pu) as additive may be those components that are different from the monomers ($\alpha 1$) and ($\alpha 2$), the crosslinkers ($\alpha 3$), and the optionally present water-soluble polymers ($\alpha 4$), and that were used in the radical polymerization. The initiators and optionally chain regulators may belong to these components.

Polymer structures that are based to at least about 50 wt %, or at least about 70 wt % or at least about 90 wt % of carboxylate groups-carrying monomers used as water-absorbing, untreated polymer structure (Pu). The component ($\alpha 1$) may include to at least about 50 wt %, or at least about 70 wt % of acrylic acid, which may be neutralized to at least about 20 mol %, or to at least about 50 mol %, or within a range from about 60 mol % to about 85 mol %.

The water-absorbing, untreated polymer structure (Pu) may be prepared from the above-mentioned monomers, comonomers, crosslinkers, water-soluble polymers, and additives by various polymerization methods. Bulk polymerization, which preferably occurs in knead reactors such as extruders, solution polymerization, spray polymerization, inverse emulsion polymerization, and inverse suspension polymerization can, for example, be mentioned in this context.

The solution polymerization is preferably carried out in water as solvent. The solution polymerization can occur continuously or discontinuously. A broad range of possible variations with respect to reaction conditions such as temperatures, type, and amount of the initiators as well as the reaction solution can be found in the state of the art. Typical processes are described in the following patent texts: U.S. Pat. No. 4,286,082, DE 27 06 135, U.S. Pat. No. 4,076,663, DE 35 03 458, DE 40 20 780, DE 42 44 548, DE 43 23 001, DE 43 33 056, and DE 44 18 818, and are well known by those of ordinary skill in the art.

In the inverse suspension or emulsion polymerization, an aqueous, partially neutralized acrylic acid solution is dispersed with the aid of protective colloids or emulsifiers in a hydrophobic organic solvent and the polymerization started by radical initiators. After ending the polymerization, the water is removed azeotropically from the reaction mixture and the polymer product filtered away and dried. The crosslinking reaction can occur by the polymerizing in of a polyfunctional crosslinker which is dissolved in the monomer solution, and/or by the reaction of suitable crosslinking agents with functional groups of the polymers during one of the production steps. The principle of the process is described, for example, in U.S. Pat. No. 4,340,706, DE 37 13 601, and DE 28 40 010.

The polymerization is started by means of an initiator, as is commonly the case. As initiator for the initiation of the polymerization, all initiators which form radicals under the polymerization conditions can be used, which are commonly used in the production of superabsorbers. An initiation of the polymerization through the action of electron beams on the polymerizable, aqueous mixture is possible. The polymerization can also be started in the absence of initiators of the above-mentioned type by the action of energetic radiation in the presence of photo-initiators. Polymerization initiators can be dissolved or dispersed in a solution of monomers according to the invention. As initiators, all compounds known to the skilled person which decompose into radicals are considered. In particular, those initiators which have already been mentioned in WO-A-2004/037903 as possible initiators fall into this group.

For the production of the water-absorbing polymer structures (Pu), a redox system consisting of hydrogen peroxide, sodium peroxodisulfate, and ascorbic acid may be used.

The drying of the hydrogel obtained after the polymerization preferably occurs at temperatures which generally lie within the range from about 80 to about 200° C. The drying may occur in ovens or dryers known to the skilled person, for example, in belt dryers, chamber dryers, rotary ovens, fluidized bed dryers, plate dryers, paddle dryers, or infrared dryers. If the thus-obtained, dried polymers are not yet present in particulate form, they should be comminuted after the drying. The comminution may occur by dry milling, or by dry milling in a hammer mill, in a pinned disc mill, in a ball mill, or in a roller mill. After the comminution, the polymer structure may be sieved to a particle size determined by sieve analysis of up to about 1,000 μm, or up to about 850 μm, whereby the weight average of the particle size may lie within a range from about 150 to about 850 μm, or from about 200 to about 600 μm.

The untreated water-absorbing polymer structure (Pu) used in process step I may be a crosslinked polyacrylate in particulate form, which has been obtained by polymerization of an acrylic acid in the presence of a crosslinker mentioned in WO-A-2004/037903 in aqueous solution, comprising the acrylic acid in an amount within a range of about 5 to about 80 wt %, or from about 10 to about 70 wt %, or from about 20 to about 50 wt %, based on the weight of the aqueous solution, and subsequent comminution of the obtained hydrogel, drying of the comminuted hydrogel to a water content within a range from about 1 to about 50 wt %, or from about 2.5 to about 40 wt %, or from 5 to about 30 wt %, or optionally further milling of the dried hydrogel.

The untreated water-absorbing polymer structure (Pu) used in process step II may be characterized by at least one of the following properties:

(A) The maximum absorption according to ERT 440.2-02 (in the case of particles, determined for the whole particle size fraction) of 0.9 wt % NaCl solution lies within a range from at least about 10 to about 1,000 g/g, or from about 20 to about 500 g/g, or from about 50 to about 250 g/g, (B) the extractable part according to ERT 470.2-02 after 16 hours (in the case of particles, determined for the whole particle size fraction) is less than about 30 wt %, or less than about 20 wt %, or less than about 15 wt %, respectively based on the untreated water-absorbing polymer structure (Pu), (C) the bulk density according to ERT 460.2-02 (in the case of particles, determined for the whole particle size fraction) may lie within the range from about 300 to about 1,000 g/l, or within the range from about 400 to about 900 g/l, or from about 500 to about 800 g/l, (D) the pH value according to ERT 400.2-02 (in the case of particles, determined for the whole particle size fraction) of 1 g of the water-absorbing polymer precursor in 1 l water lies within the range from about 4 to about 10, or from about 4.5 to about 9, or from about 5 to about 8, (E) the SFC value determined according to the herein-described test method is at most about $40 \times 10^{-7}$ s×cm$^3$/g, or at most about $30 \times 10^{-7}$ s×cm$^3$/g, or at most about $20 \times 10^{-7}$ s×cm$^3$/g, or at most about $10 \times 10^{-7}$ s×cm$^3$/g, or at most about $5 \times 10^{-7}$ s×cm$^3$/g, (F) The absorption against a pressure of 50 g/cm$^2$ determined according to ERT 442.2-02 (in the case of particles, determined for the whole particle size fraction) lies within a range from about 10 to about 26 g/g, or from about 13 to about 25 g/g, or from about 15 to about 24 g/g.

According to a particular embodiment of the process according to the invention, polymer structures may be provided in process step I that are characterized by the following properties or property combinations: (A), (B), (C), (D), (E), (F), (A)(E), (B)(E), (C)(E), (D)(E), (E)(F), (B)(E), (B)(F), (B)(E)(F), whereby (B), (E), (F) and (E)(F) and (B)(E)(F) are desirable.

It is further preferred that the untreated water-absorbing polymer structures (Pu) used in process step II, if the polymer structures are particles, are based to at least about 30 wt %, or at least about 40 wt %, or at least about 50 wt % on particles with a particle size within a range from about 300 to about 600 μm.

In process step II of the process according to the invention, the untreated water-absorbing polymer structures (Pu) may be brought into contact with a permeability-increasing agent, whereby the permeability-increasing agent may be brought into contact with the polymer structure (Pu) in an amount of at least 0.001 wt. %, or from about 0.1 to about 10 wt %, or from about 0.5 to about 5 wt %, based upon the weight of the untreated water-absorbing polymer structure (Pu). This permeability-increasing agent may be a SiO compound, a salt comprising a multivalent, or a trivalent cation, or a mixture of a SiO compound and a salt comprising a multivalent.

As SiO compound may include SiO compounds that influence the permeability properties of the water-absorbing untreated polymer structures. The SiO compounds may include compounds that are obtainable by polycondensation of the monosilicic acid, as well as silicates. Examples of polysilicic acids are silica sols, as described in DE 102 49 821. Silicates may include scaffold silicates such as zeolites or silicates which have been obtained by drying aqueous silicic acid solutions or silica sols, for example the commercially available pyrogenic silicic acids known under the description Aerosil®. Such silicates may have a particle size of from about 5 to about 50 nm, or from about 8 to about 20 nm. SiO compounds may include precipitated silicic acids, as commercially obtainable, for example under the name Sipernat®. Preferred silicates may include natural or synthetic silicates which are disclosed as silicates in "Holleman and Wiberg, Lehrbuch der Anorganischen Chemie", Walter de Gruyter-Verlag, 91.-100. Auflage, 1985) on pages 750 to 783.

Zeolites may include natural zeolites from the natrolite groups, the harmotone groups, the modenite groups, the chabasite groups, the faujasite groups (sodalite groups), or the analcite groups. Examples of natural zeolites are Analcime, Leucite, Pollucite, Wairakite, Bellbergite, Bikitaite, Boggsite, Brewsterite, Chabazite, Willhendersonite, Cowlesite, Dachiardite, Edingtonite, Epistilbite, Erionite, Faujasite, Ferrierite, Amicite, Garronite, Gismondine, Gobbinsite, Gmelinite, Gonnardite, Goosecreekite, Harmotome, Phillipsite, Wellsite, Clinoptilolite, Heulandite, Laumontite, Levyne, Mazzite, Merlinoite, Montesommaite, Mordenite, Mesolite, Natrolite, Scolecite, Offretite, Paranatrolite, Paulingite, Perlialite, Barrerite, Stilbite, Stellerite, Thomsonite, Tschernichite, or Yugawaralite. Preferred synthetic zeolites are zeolite A, zeolite X, zeolite Y, zeolite P, or the product ABSCENTS.

SiO compounds may include pyrogenic silica, as is, for example, obtainable under the trade name Aerosil®, precipitation silicates, as commercially obtainable under the name Sipernat®, or silica sols, as, for example, obtainable under the trade name Levasil®.

The SiO compound may be brought into contact in an amount from at least 0.001 wt %, or from about 0.1 to about 10 wt %, or from about 0.5 to about 5 wt %, based on the untreated, water-absorbing polymer structure (Pu), with the untreated, water-absorbing polymer structure, whereby the bringing into contact may occur in such a way that the SiO compound is brought into contact with the untreated water-absorbing polymer structure (Pu) either under dry conditions or in the form of a fluid $F_1$ comprising the SiO compound and a solvent, such as water, organic solvents which are miscible with water such as methanol, ethanol, 1-propanol, 2-propanol, n-butanol, sec-butanol, tert-butanol, or a mixture of at least two of these solvents, whereby the bringing into contact preferably occurs by spraying the polymer particles with the fluid $F_1$ and combining. If the SiO compound is used in the form of a fluid $F_1$, at most about 10 wt %, or at most about 7 wt %, or at most about 5 wt % of solvent may be used, based upon the weight of the untreated, water-absorbing polymer structure (Pu). The SiO compound in the form of an aqueous solution may be substantially free from organic solvents, in particular free from polyvalent alcohols and polyalkylene glycol ethers, particularly preferably free from diethylene glycol monomethylether and 1,3-butanediol, may be brought into contact with the untreated water-absorbing polymer structure (Pu).

Salts comprising a multivalent, or trivalent cation, or salts may be used which comprise $Al^{3+}$ ions. Among these salts, may be salts comprising chloride anions, iodide anions, bromide anions, nitrate anions, nitrite anions, sulphide anions, sulfite anions, sulfate anions, carbonate anions, hydrogen carbonate anions, hydroxide anions, acetate anions or oxalate anions. Preferred salts include aluminum chloride, polyaluminum chloride, aluminum sulfate, aluminum nitrate, bis-aluminium potassium sulfate, bis-aluminium sodium sulfate, aluminum lactate, aluminum oxalate, aluminum citrate, aluminum glyoxylate, aluminum succinate, aluminum itaconate, aluminum crotonate, aluminum butyrate, aluminum sorbate, aluminum malonate, aluminum benzoate, aluminum tartrate, aluminum pyruvate, aluminum valerate, aluminum formate, aluminum glutarate, aluminum propanate, or aluminum acetate, whereby $AlCl_3 \times 6H_2O$, $NaAl(SO_4)_2 \times 12H_2O$, $KAl(SO_4)_2 \times 12H_2O$, or $Al_2(SO_4)_3 \times 14\text{-}18H_2O$ and the corresponding anhydrous salts, $MgSO_4 \times 10H_2O$ or anhydrous magnesium sulfate are desirable salts.

With respect to the salt comprising a multivalent, or trivalent cation, the amount of salt in an amount from at least about 0.001 wt %, or from about 0.1 to about 10 wt %, or in an amount from about 0.5 to about 5 wt %, respectively based on the weight of the untreated water-absorbing polymer structure (Pu), is brought into contact with the untreated water-absorbing polymer structure (Pu).

The bringing into contact of the untreated water-absorbing polymer structure (Pu) with the salt comprising a multivalent, such as a trivalent cation, may occur by bringing the untreated water-absorbing polymer structure (Pu) into contact with the salt under dry conditions or in the form of a fluid $F_2$ comprising the salt and a solvent, such as water, organic solvents which are miscible with water such as methanol, ethanol, 1-propanol, 2-propanol, n-butanol, sec-butanol, tert-butanol, or a mixture of at least two of these solvents, whereby the bringing into contact may occur by spraying the polymer particles with the fluid $F_2$ and combining The salt in the form of an aqueous solution, which may be free from organic solvents, or free from multivalent alcohols and polyalkylene glycol ethers, or free from diethylene glycol monomethyl ether and 1,3-butanediol, may be brought into contact with the untreated, water-absorbing polymer structures (Pu).

In this context, the bringing into contact of the untreated water-absorbing polymer structure (Pu) with the fluid $F_2$ comprising the salt may occur in a two-step process. The two-step process may comprise a first mixing, in which a plurality of absorbent polymer structures may be mixed with the fluid, and a second mixing, in which the fluid may be homogenized inside the polymer particles, whereby the polymer particles in the first mixing may be mixed with a speed such that the kinetic energy of the individual polymer particles may be, on average, larger than the adhesion energy between the individual polymer particles, and the polymer particles in the second mixing are mixed with a lower speed than in the first mixing.

If the untreated water-absorbing polymer structure (Pu) is brought into contact with both the SiO compound as well as with the salt comprising the multivalent, or trivalent cation,
i) the untreated, water-absorbing polymer structure (Pu) may be brought into contact with both components one after the other, whereby the bringing into contact of the individual components can occur under dry conditions or in the form of a fluid,
ii) the untreated water-absorbing polymer structure (Pu) may be brought into contact with both components at the same time, in that, for example, both components are first combined under dry conditions, and then this mixture is brought into contact with the untreated water-absorbing polymer structure (Pu), or in that both components in the form of a common fluid are brought into contact with the untreated, water-absorbing polymer structure (Pu).

The bringing into contact of the untreated, water-absorbing polymer structure (Pu) with the SiO compounds, with the salt comprising the multivalent, or trivalent cation, or with the mixture of two of these components under dry conditions or in the form of a fluid may occur in mixing aggregates known to the skilled person such as, e.g., the Patterson-Kelley mixer, the DRAIS turbulence mixer, the Lödige mixer, the Ruberg mixer, the screw mixer, the plate mixer, and the fluidized bed mixer as well as in continuously operating vertical mixers, in which the polymer structure is mixed at high frequency by means of rotating knives (Schugi mixer).

If a surface post-crosslinking is not carried out during process step II, the bringing into contact of the untreated, water-absorbing polymer structure (Pu) with the SiO compounds, with the salt comprising a multivalent, or trivalent cation, or with the mixture of two of these components may occur at temperatures within a range from about 10 to about 100° C., or from about 15 to about 60° C., or from about 20 to about 40° C., or at room temperature.

Furthermore, the water-absorbing polymer structures obtainable by the process according to the invention may be surface post-crosslinked. The surface post-crosslinking may occur before, during, or after process step II, wherein chemical post-crosslinkers may be used for the post-crosslinking.

Chemical post-crosslinkers may include compounds that have at least two functional groups that can react with functional groups of a polymer in a condensation reaction, i.e., condensation crosslinker, in an addition reaction or in a ring opening reaction.

Crosslinking agents may be polyols, for example ethylene glycol, polyethylene glycols such as diethylene glycol, triethylene glycol and tetraethylene glycol, propylene glycol, polypropylene glycols such as dipropylene glycol, tripropylene glycol or tetrapropylene glycol, 1,3-butanediol, 1,4-butanediol, 1,5-pentanediol, 2,4-pentanediol, 1,6-hexanediol, 2,5-hexanediol, glycerine, polyglycerine, trimethylolpropane, polyoxypropylene, oxyethylene-oxypropylene block copolymers, sorbitan fatty acid esters, polyoxyethylene sorbitan fatty acid esters, pentaerythritol, polyvinyl alcohol and sorbitol, aminoalcohols, for example ethanolamine, diethanolamine, triethanolamine or propanolamine, polyamine compounds, for example ethylenediamine, diethylenetriamine, triethylenetetramine, tetraethylenepentamine or pentaethylene-hexamine, polyglycidyl ether compounds such as ethylene glycol diglycidyl ether, polyethylene glycol diglycidyl ether, glycerol diglycidyl ether, glycerol polyglycidyl ether, pentaerythritol polyglycidyl ether, propylene glycol diglycidyl ether, polypropylene glycol diglycidyl ether, neopentyl glycol diglycidyl ether, hexanediol glycidyl ether, trimethylolpropane polyglycidyl ether, sorbitol polyglycidyl ether, phthalic acid diglycidyl ester, adipic acid diglycidyl ether, 1,4-phenylene-bis(2-oxazoline), glycidol, polyisocyanates, preferably diisocyanates such as 2,4-toluene diisocyanate and hexamethylene diisocyanate, polyaziridine compounds such as 2,2-bishydroxymethyl-butanol-tris[3-(1-aziridinyl)propionate], 1,6-hexamethylene-diethylene urea and diphenylmethane-bis-4,4'-N,N'-diethylene urea, halogen epoxides, for example epichlorohydrin, epibromohydrin and α-methylepichlorohydrin, alkylene carbonates such as 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1, 3-dioxan-2-one, 1,3-dioxolan-2-one, poly-1,3-dioxolan-2-one, polyquaternary amines such as condensation products of dimethylamines and epichlorohydrin. Post-crosslinkers may further include polyoxazolines such as 1,2-ethylenebisoxazoline, crosslinking agents with silane groups such as γ-glycidoxypropyltrimethoxysilane and γ-aminopropyltrimethoxysilane, oxazolidinones such as 2-oxazolidinone, bis- and poly-2-oxazolidinones, and diglycol silicates.

The post-crosslinker may be used in the process according to the invention in an amount within the range from about 0.01 to about 30 wt %, or from about 0.1 to about 20 wt %, or from about 0.3 to about 5 wt %, based upon the water-absorbing polymer structure.

In particular, if the post-crosslinker is not liquid under the pressure and temperature conditions of the post-crosslinking, the post-crosslinker may be used in the form of a fluid $F_3$ comprising the post-crosslinker and a solvent, whereby as solvent, such as water, organic solvents which are miscible with water such as, for example, methanol, ethanol, 1-propanol, 2-propanol or 1-butanol, or mixtures of water and these organic solvents is used. The post-crosslinker, if it is used together with a solvent, is comprised in the fluid $F_3$ preferably in an amount within a range from about 5 to about 75 wt %, or in an amount from about 20 to about 40 wt %, or in an amount from about 5 to about 25 wt %, respectively based upon the total weight of the fluid $F_3$.

The bringing into contact of the fluid $F_3$ with the water-absorbing polymer structure preferably may occur in the mixing aggregates mentioned in connection with the bringing into contact of the untreated water-absorbing polymer structure (Pu) with the SiO compound or respectively with the salt comprising a multivalent, preferably trivalent cation.

After the post-crosslinker or the fluid $F_3$ respectively has been brought into contact with the water-absorbing polymer structures, the post-crosslinking reaction occurs by heating the water-absorbing polymer structure to temperatures from about 40 to about 300° C., or from about 80 to about 275° C., or from about 125 to about 250° C. The optimal duration of the post-crosslinking may be determined for the individual post-crosslinker types. It may be limited if the desired property profile of the water absorbing polymer structure is degraded again as a result of heat damage. The thermal treatment may be carried out in commonly available dryers or ovens. Examples that may be mentioned are rotary ovens, fluidized bed dryers, plate dryers, pedal dryers, or infrared dryers.

If the post-crosslinking occurs before process step II, the untreated water-absorbing polymer structures may be first post-crosslinked in the above described way. The post-crosslinked polymer structures may then be brought into contact with the SiO compound with the salt comprising a multivalent, or trivalent cation, or with a mixture of the SiO compound and the salt in the above-described way according to process step II.

If the post-crosslinking occurs during process step II, the post-crosslinker may be brought together with the SiO compound, the salt comprising the multivalent, or trivalent cations, or the mixture of the SiO compound and the salt into contact with the untreated, water-absorbing polymer structure (Pu). If the bringing into contact of the polymer structures with the SiO compound or with the salt does not occur under dry conditions, the post-crosslinker may also be dissolved or dispersed in the fluid $F_1$ or in the fluid $F_2$. After the bringing into contact of the untreated water-absorbing polymer structure (Pu) with the fluid $F_1$ or $F_2$ respectively, the post-crosslinking of the polymer structures may occur by heating to the above-mentioned temperatures.

If the post-crosslinking occurs after process step II, the untreated water-absorbing polymer structures (Pu) may be first brought into contact in the above-described way with the SiO compound, with the salt comprising a multivalent, or trivalent cation or with the mixture of the SiO compound and the salt. The surface post-crosslinking may occur by the bringing into contact of the polymer structures with the post-crosslinker and subsequent heating.

According to a particular embodiment of the process according to the invention for production of water-absorbing polymer structures, in process step i) an untreated, however, already surface post-crosslinked water-absorbing polymer structure may be brought into contact with the permeability-increasing agent, whereby the permeability-increasing agent is present in the form of powder.

In this particular embodiment of the process according to the invention for the production of water-absorbing polymer structures, the process may comprise the following process steps:

i) providing the untreated, preferably, however, already surface post-crosslinked water-absorbing polymer structure; and ii) bringing into contact of the untreated, preferably, however, already surface post-crosslinked water-absorbing polymer structure with a fine particulate component comprising a SiO compound, a salt, comprising a multivalent, preferably trivalent, cation or a mixture of a SiO compound and a salt comprising a multivalent, preferably trivalent cation, preferably at a temperature from about 30 to about 300° C., or from about 100 to 300° C., or from about 125 to 250° C., or from about 150 to about 200° C.

In this context, at least about 50 wt %, or at least about 75 wt %, or at least about 95 wt %, or at least about 99 wt % of the salt which may be present in powder form comprising a multivalent, or trivalent cation, having an average particle diameter from about 10 to about 1000 μm, or from about 50 μm to about 800 μm, or from about 100 to about 600 μm, or from about 200 to about 400 μm (weight average), respectively determined by means of processes known to the skilled person for determination of particle size, for example by sieve analysis or by means of a Coulter counter. At least about 50 wt %, or at least about 75 wt %, or at least about 90 wt % of the SiO compound may have a particle size determined by sieve analysis (for particle sizes larger than 10 μm) or laser diffractometry (for particle sizes smaller than 10 μm) from about 10 to about 1,000,000 nm, or within a range from about 12 to about 500,000 nm, or from about 15 to about 5,000 nm. The SiO compound may have a weight average of the particle size from about 15 to about 5,000 nm, or from about 20 to about 3000 nm, or from about 100 to about 2,000 nm.

Furthermore, the fine particulate component, in addition to the powdery salt, the powdery SiO compound, or the powdery mixture of the salt and the SiO compound, additionally comprises a binder, whereby this binder may also be present in particulate form and is based in particular to at least about 50 wt %, or at least about 75 wt %, or to at least about 95 wt %, or to at least about 99 wt % on particles with an average particle size from about 10 to about 1,000 μm, or from about 50 µm to about 800 µm, or from about 100 to about 600 µm, or from about 200 to about 400 µm (weight average), respectively determined by processes known to the skilled person for particle size determination, for example by sieve analysis or by means of a Coulter counter.

In this context, the binder comprises as binder principal component an organic compound, whereby the organic compound may be a solid at about 20° C.

The organic compound may be a linear polymer, or a linear polymer selected from the group comprising polyurethanes, polyesters, polyamides, polyester amides, polyolefins, polyvinylesters, polyethers, polystyrenes, polyimides, in particular polyether imides, polyimines, sulphur polymers, in particular polysulfones, polyacetals, in particular polyoxymethylenes, fluorine-plastics, in particular polyvinylidene fluoride, styrene-olefin-copolymers, polyacrylates, ethylene-vinylacetate copolymers, or mixtures of two or more of the polymers mentioned.

Particularly suitable linear polyethers may comprise polyalkylene glycols, in particular polyethylene glycols, polypropylene glycols, poly(ethylene/propylene)glycols with statistical or block-like arrangement of the ethylene or propylene monomers or mixtures of at least two of these polyalkylene glycols.

Further suitable, linear polymers may include those polymers which are mentioned in DE-A-103 34 286 as "thermoplastic adhesives" ("thermoplastische Klebstoffe"). The disclosure of DE-A-103 34 286 concerning thermoplastic adhesives is hereby introduced as reference.

If a binder is used in addition to the SiO compound and/or the salt, it is preferred that the bringing into contact of the surface of the untreated, already surface post-crosslinked water-absorbing polymer structure with the fine particulate components may occur at a temperature from about 30 to about 200° C., or from about 50 to about 160° C., or from about 70 to about 140° C. These temperatures may lead to an immobilization of the fine particulates on the surface of the untreated water-absorbing polymer structure.

The amount of the binding agent, if used, may lie from about 0.0001 to about 5 wt %, or from about 0.001 to about 2 wt %, respectively based on the weight of the water-absorbing polymer structure. The weight ratio between fine particulate component and binder may lie within a range of fine particulate component:binder from about 20:1 to about 1:20, or from about 10:1 to about 1:10, or from about 10:1 to about 2:1.

In the above-described, particular embodiment of the process according to the invention, in which a powdery SiO compound, a powdery salt comprising a multivalent, or trivalent cation, or a powdery mixture of these components may be used, the process also may comprise, in addition to the provision of the untreated, preferably already surface post-crosslinked water-absorbing polymer structure, in process step i) the provision of a fine particulate component comprising the powdery SiO compound, the powdery salt comprising a multivalent, preferably trivalent cation or the powdery mixture of these components as well as the powdery binder. With respect to the method of bringing into contact of the fine particulate component with the untreated water-absorbing polymer structure, different processes are conceivable:

According to variant $V_A$, in process step ii), firstly a mixture of fine particulate component and untreated, surface post-crosslinked water-absorbing polymer structures may be prepared, and this is then heated at the above-mentioned temperatures to cause an immobilization of the fine particulates, whereby the water-absorbing polymer structure may already be surface post-crosslinked, whereby the water-absorbing polymer structure has already been brought into contact with the post-crosslinker, but has not yet been heated to a temperature necessary for a surface post-crosslinking.

According to variant $V_B$, firstly, before process step ii), the untreated, surface post-crosslinked water-absorbing polymer structures may be heated to the above-described temperature, and then in process step ii) these pre-heated water-absorbing polymer structures are combined with the non-pre-heated fine particulate component.

According to variant $V_C$, firstly, before process step ii), the untreated, surface post-crosslinked water-absorbing polymer structures and the fine particulate components may respectively be separately heated to the above-described temperature, and then in process step ii), the pre-heated water-absorbing polymer structures may be combined with the likewise pre-heated fine particulate component. According to a particular embodiment of this variant $V_C$, the fine particulate component may be first cooled after the heating and before the combining with the pre-warmed water-absorbing polymer structures, at a temperature from about 10 to about 100° C., or from about 15 to about 75° C., or from about 20 to about 60° C., afterwards optionally to comminute, for example using a pestle and mortar, and then to combine the cooled and optionally comminuted fine particulate component with the pre-warmed water-absorbing polymer structures.

According to variant $V_D$, firstly, before process step ii), the fine particulate components are heated to the above-described temperature, and then in process step ii) the pre-heated fine particulate component may be combined with the non-pre-heated, untreated, surface post-crosslinked water-absorbing polymer structures. According to a particular embodiment of this variant $V_D$, it is desirable first to cool the fine particulate component after the heating and before the combining with the not pre-warmed water-absorbing polymer structures, preferably to a temperature from about 10 to about 100° C., or from about 15 to about 75° C., or from about 20 to about 60° C., afterwards optionally to comminute, for example using a pestle and mortar, and then to combine the cooled and optionally comminuted fine particulate component with the not pre-warmed water-absorbing polymer structures.

Furthermore, it may be advantageous in respect of the above described particular embodiment of the process according to the invention, in which a powdery SiO compound, a powdery salt, comprising a multivalent, or trivalent cation, or a powdery mixture of these components is used, if a further process step iii), in which the mixture of untreated, water-absorbing polymer structure and fine particulate components is further mixed for a time from about 10 minutes to about 5 hours, or from about 30 minutes to about 3 hours, follows process step ii), in order to enable as homogeneous a distribution as possible of the fine particulates and the absorbent polymer structure. Mixing devices known to the skilled person may be used. In this further process step, the mixture of untreated, water-absorbing polymer structure and fine particulate component may be introduced into the mixer with the temperature which it has after the immobilization in process step ii), whereby the mixture can then be cooled during the mixing, preferably constantly to a lower temperature, preferably to room temperature.

A further contribution to the solution of the above-mentioned objects may be provided by a water-absorbing polymer structure having the following properties:

a. a retention determined according to the test methods described herein of at least about 32 g/g, or at least about 33 g/g, or at least about 34 g/g, or at least about 35 g/g, or at least about 36 g/g, or at least about 37 g/g, or at least about 38 g/g, or at least about 40 g/g, or from about 33.2 to about 45 g/g, or from about 34 to 40 g/g; and b. a Time-dependent Absorption Against Pressure against a pressure of 20 g/cm$^2$ (TAAP at 0.3 psi) determined according to the test methods described herein selected from the group consisting of:
  b1. 50% of the maximum absorption of the polymer structures within about 20 minutes, or within about 15 minutes, or within about 10 minutes; and
  b2. 90% of the maximum absorption of the polymer structures within about 40 minutes, or about 30 minutes, or within about 20 minutes.

Water-absorbing polymer structures with the above-described absorption properties a. and b. may, for example, be obtainable by the above-described process according to the invention. Accordingly, the water-absorbing polymer structures according to the invention may be fiber, foams, or particles, whereby fibers and particles are preferred and particles are particularly preferred. The fibers or the particles respectively have the respective fiber dimensions or particle size distribution mentioned above in connection with the inventive process for production of water-absorbing polymers.

Furthermore, the water-absorbing polymer structures according to the invention, as well as the water-absorbing polymer structures obtainable by the inventive process, may be characterized in that a permeability-increasing agent in an amount of at least about 0.001 wt %, or from about 0.1 to about 10 wt %, or from about 0.5 to about 5 wt % may be immobilized on the surface of the polymer structures. This permeability-increasing agent may be
  a SiO compound or
  a salt comprising a multivalent, preferably trivalent cation or
  a mixture of a SiO compound and a salt comprising a multivalent or trivalent cation.

SiO compounds and salts comprising a multivalent or trivalent cation may be those SiO compounds and salts that have already been mentioned above in connection with the process according to the invention for the production of water-absorbing polymer structures.

According to a particular embodiment of the water-absorbing polymer structures according to the invention, the polymer structures may be polymer particles that have a particle size determined by sieve analysis from about 10 to about 3000 μm, or from about 20 to about 2000 μm, or from about 150 to about 850 μm, whereby the polymer particles may be based to at least about 50 wt %, to at least about 70 wt %, or to at least about 90 wt % on carboxylate groups-comprising monomers, or acrylic acid, whereby these carboxylate groups-comprising monomers may be neutralized to at least about 20 mol %, or to at least about 50 mol %, or from about 60 to about 85 mol %. The water absorbing polymer structures according to the invention, if the polymer structures are particles, may be based to at least about 30 wt %, or to at least about 40 wt %, or to at least about 50 wt % on particles with a particle size from about 300 to about 600 μm.

The water-absorbing polymer structures may have an absorption against a pressure of 0.7 psi (50 g/cm$^2$) determined according to ERT 442.2-02 of at least about 10 g/g, or at least about 12 g/g, or at least about 14 g/g, or at least about 15 g/g, whereby a value of about 35 g/g, or about 30 g/g is not exceeded (in the case of particles, respectively determined for the total particle fraction).

The water-absorbing polymer structures may be further characterized by an SFC value determined according to the test method described herein of at most about $40 \times 10^{-7}$ s×cm$^3$/g, or at most about $30 \times 10^{-7}$ s×cm$^3$/g, or at most about $20 \times 10^{-7}$ s×cm$^3$/g, or at most $10 \times 10^{-7}$ s×cm$^3$/g, or at most about $5 \times 10^{-7}$ s×cm$^3$/g.

The water-absorbing polymer structures may be further characterized in that an airlaid composite produced according to the test methods described herein consisting of about 350 g/m$^2$ cellulose fiber, about 18 g/m$^2$ of a bicomponent fiber, about 350 g/m$^2$ of the water-absorbing polymer structures according to the invention, and about 36 g/m$^2$ tissue may be characterized by at least one of the following properties:

(γ1) a Rewet value determined according to the test method described herein after the third wetting of at most about 3 g, or at most about 2.9 g, or at most about 2.8 g;

(γ2) an Acquisition Time determined according to the test method described herein after the second wetting of at most about 450 s, or at most about 400 s, or at most about 380 s;

(γ3) an Acquisition Time determined according to the test method described herein after the third wetting of at least about 1500 s, or at most about 1400 s, or of at most about 1300 s.

According to a particular embodiment of the water-absorbing polymer structure according to the invention, an airlaid composite prepared according to the test method described herein may be characterized by the following properties or combinations of properties: (γ1), (γ2), (γ3), (γ1)(γ2), (γ1)(γ3), (γ2)(γ3), (γ1)(γ2)(γ3).

A further contribution to the solution of the above-mentioned objects may be provided by a composite comprising the above-defined water-absorbing polymer structures or the water-absorbing polymer structures obtainable by the process according to the invention and a substrate. The water-absorbing polymer structures according to the invention and the substrate may be thermally bound with each other. Substrates may be sheets made from polymers, such as, for example, from polyethylene, polypropylene or polyamide, metals, non-wovens, fluff, tissues, woven materials, natural or synthetic fibers, or other foams. Furthermore, the composite according to the invention can also comprise, in addition to the water-absorbing polymer structures according to the invention and the substrate, additives, such as, for example, thermoplastic materials.

According to a preferred embodiment of the composite according to the invention, the composite is an absorbent layer, a core, or a wipe.

If the composite according to the invention is an absorbent layer, this advantageously may have at least one of the following properties:

(δ1) a Rewet value determined according to the test method described herein after the third wetting of at most about 3 g, or at most about 2.9 g, or at most about 2.8 g;

(δ2) an Acquisition Time determined according to the test method described herein after the second wetting of at most about 450 s, or at most about 400 s, or at most about 380 s;

(δ3) an Acquisition Time determined according to the test methods described herein after the third wetting of at most about 1500 s, at most about 1490 s, or at most about 1480 s.

According to another embodiment of the absorbent layer according to the invention, this may be characterized by the following properties or property combinations: (δ1), (δ2), (δ3), (δ1)(δ2), (δ1)(δ3), (δ2)(δ3), (δ1)(δ2)(δ3).

Absorbent layers according to the invention may be those absorbent layers that are described in U.S. Pat. No. 5,599,335 as "absorbent members", whereby U.S. Pat. No. 5,599,335 is hereby introduced as a reference limited to absorbent members and the disclosure of U.S. Pat. No. 5,599,335, in particular concerning the fibers and additives comprised in the absorbent layers, as well as concerning the process of production of the absorbent layers.

This composite or this absorbent layer may comprise at least one region which comprises the water-absorbing polymer structures according to the invention in an amount from about 15 to 100 wt %, or from about 30 to about 100 wt %, or from about 50 to 99.99 wt %, or from about 60 to 99.99 wt %, or from about 70 to about 99 wt %, respectively based on the total weight of the concerned region of the composite or of the absorbent layer respectively, whereby this region preferably has a size of at least about 0.01 cm$^3$, or at least about 0.1 cm$^3$ or at least about 0.5 cm$^3$.

The absorbent layer may be characterized by a mass per unit area of at least about 0.02 g/cm$^2$, or at least about 0.03 g/cm$^2$, or from about 0.02 to about 0.12 g/cm$^2$, or from about 0.03 to about 0.11 g/cm$^2$, whereby the absorbent layer further has a thickness of at most about 20 mm, or at most about 15 mm, or at most about 10 mm.

The absorbent layer according to the invention may have a surface area of at most about 500 cm$^2$, or at most about 350 cm$^2$, or at most about 300 cm$^2$.

The production of the composite according to the invention preferably may occur by bringing the water-absorbing polymer structure according to the invention or the water-absorbing polymer structures obtainable by the process according to the invention and the substrate, and optionally the additive, into contact with each other. The bringing into contact preferably occurs by wetlaid and airlaid processes, compacting, extruding, and mixing.

According to another embodiment of the process according to the invention for producing a composite, this process comprises the following process steps:
A) provision of a substrate;
B) provision of an untreated, preferably, however, already surface post-crosslinked water-absorbing polymer structure;
C) providing a fine particulate component;
D) bringing into contact of the substrate with the water-absorbing polymers structure
E) bringing into contact of the water-absorbing polymer structure with the fine particulate component;
F) immobilization of at least a part of the fine particulates on the surface of the water-absorbing polymer structures.

As fine particulate component includes all fine particulate components that have already been described above in connection with the particular embodiment of the process according to the invention for production of water-absorbing polymer structure, in which a powdery SiO compound and/or a powdery salt is used. Another embodiment includes a mixture of powdery SiO compound, powdery salt, or powdery mixture of these two components and powdery binder.

According to a variant of this particular embodiment of the inventive process for production of a composite, first the substrate and the water-absorbing polymer structure are brought into contact with each other, such as by first providing the substrate and then applying, or sprinkling the polymer structure either uniformly or on defined areas of the substrate surface. The water-absorbing polymer structures situated on the substrate surface may then be brought into contact with the fine particulate component, for example by sprinkling the fine particulate component on the surface post-crosslinked polymer structure situated on the substrate surface. The immobilization of the fine particulate components on the surface of the polymer structure may then occur, whereby this immobilization may occur by the heating described above in connection with the inventive process for treatment of the surface of water-absorbing polymer structures. In this variant of the particular embodiment of the inventive process for production of a composite, process step E) therefore occurs after process step D).

According to another variant of this particular embodiment of the inventive process for production of a composite, first the substrate is provided. Then the surface post-crosslinked polymer structure may be brought into contact with the substrate, such as by first providing the substrate and then applying, or sprinkling, the surface post-crosslinked polymer structure either uniformly or on defined areas of the substrate surface. Before the polymer structure is brought into contact with the substrate surface, the water-absorbing polymer structures may be brought into contact with the fine particulate component, for example by combining the fine particulate component with the surface post-crosslinked polymer structure before it is sprinkled onto the substrate surface. After the polymer structures have been brought into contact with the substrate, the immobilization of the fine particulate component on the surface of the polymer structure occurs. In this variant of the particular embodiment of the inventive process for production of a composite, process step E) therefore occurs before process step D).

The present invention may also relate to the composite obtainable by the above-described process.

The present invention further relates to chemical products comprising the polymer structures according to the invention or the composite. Preferred chemical products are foams, formed bodies, fibers, sheets, films, cables, sealing materials, liquid-absorbing hygiene articles, carriers for plant or fungus growth regulating agent or plant protection active agents, additives for construction materials, packaging materials, or soil additives.

The invention also relates to the use of the water-absorbing polymer structures according to the invention, of the water-absorbing polymer structures obtainable by the process according to the invention, of the composite or of the composite obtainable by the above-described process in the above-mentioned chemical products, in particular in hygiene products, in combating floods, in insulation against water, for regulation of the water content of soils, or for treatment of foods.

Test Methods

Determination of the SFC Value

The determination of the permeability in the swollen state (Saline Flow Conductivity=SFC) is carried out according to a method described in WO-A-95/22356. Approximately 0.9 g superabsorber material (for particles, the total particle fraction) is weighed into a cylinder with a sieve floor and carefully distributed on the sieve surface. The superabsorber material is allowed to swell in JAYCO synthetic urine for one hour against a pressure of 20 g/cm$^2$. After determining the swell height of the superabsorber, 0.118 M NaCl solution from a graduated reservoir is allowed to run through the swollen gel layer at constant hydrostatic pressure. The swollen gel layer is covered during the measurement with a special cylinder which ensures a uniform distribution of the 0.118 M NaCl solution above the gel and constant conditions (measurement temperature 20-25° C.) during the measurement in respect of the gel bed properties. The pressure acting on the swollen superabsorber continues to be 20 g/cm$^2$. Using a computer and a balance, the amount of liquid which passes the gel layer as a function of time is determined at intervals of 20 seconds over a time of 10 minutes. The flow rate g/s through the swollen gel layer is determined by regression analysis with extrapolation of the gradient and determination of the middle point at the time point t=0 of the flow amount within the minutes 2 to 10. The SFC value (K) is given in $cm^3 \cdot s \cdot g^{-1}$ and is calculated as follows:

$$K = \frac{F_s(t=0) \cdot L_0}{r \cdot A \cdot \Delta P_1} = \frac{F_s(t=0) \cdot L_0}{139506}$$

whereby $F_S(t=0)$ is the flow rate in g/s, $L_0$ is the thickness of the gel layer in cm, r is the density of the NaCl solution (1.003 $g/cm^3$), A is the area of the upper side of the gel layer in the measuring cylinder (28.27 $cm^2$), ΔP is the hydrostatic pressure which acts upon the gel layer (4,920 $dyne/cm^2$), and K is the SFC value.

Determination of the Retention

The so-called teabag test is carried out for determining the retention of the water-absorbing polymer material (for particles, the total particle fraction). As test solution, a 0.9 wt % NaCl solution is used.

About 1 g water-absorbing polymer material is weighed into ($W_1$) and sealed in a teabag. The teabag is placed for 30 minutes in the test solution and then spun in a spinner (23 cm diameter, 1,000 rpm) for three minutes and weighed again ($W_2$). A teabag without water-absorbing polymer material, whose weight is likewise determined after the spinning ($W_3$) is run at the same time as blind value. The retention is given in g/g and calculated as follows:

$$\text{Retention [g/g]} = \frac{W_2 - W_3 - W_1}{W_1}$$

Determination of the Time-Dependent Absorption Against Pressure (TAAP)

The absorbent material to be tested is sprinkled onto the floor 3 of an apparatus 1 consisting of a Plexiglas cylinder 2, which has an inner diameter of 60 mm, a height of 50 mm and as floor 3 a sieve fabric made of steel (400 mesh), and loaded with a defined weight 4 (the weight 4 is a cylindrical stamp which can be introduced and fits exactly into the Plexiglas cylinder 2 and into which a metal weight can be introduced). The total weight of the weight 4 is selected so that a pressure of 20 $g/cm^2$ acts upon the absorbent material. The apparatus 1 is placed upon a support 6, which has a cylindrical depression 7 for a glass frit 8 with a diameter of 70 mm (porosity=0) from Schott-Keramikfilter Duran (Germany) and which is located upon a balance 5, whereby between the glass frit 8 and the sieve floor 3 of the Plexiglas cylinder 2, a filter paper 9 (Schleicher & Schull, Schwarzband 589/1, diameter 45 mm) is laid, centrally upon the filter paper 9 a further glass frit 10 with a diameter of 20 mm is laid and upon the glass frit 8 a distance ring 11 with an inner diameter of 60 mm, a thickness of 5 mm and a height which corresponds exactly to the height of the glass frit 10. The glass frit 8 is connected fluid-conductingly by means of a silicone tube 12 with a liquid reservoir 13 (which is a 500 ml dropping funnel with a glass tube), in which reservoir is located 0.9 wt. % NaCl solution. Furthermore, by means of valves 14 and 15, the transport of the NaCl solution from the liquid reservoir 13 to depression 7 and thus to the glass frit 8 can be selectively opened or closed.

First, without the apparatus 1 being on the support 6 and the glass frit 8 in the depression 7 of the support 6, valves 14 and 15 are opened, whereby the liquid reservoir is preferably at such a height that the depression 7 is filled to the edge with the test liquid. Then the glass frit 8 is placed into the depression 7 and the filter paper 9 is laid upon the glass frit 8, whereby it is ensured that the glass frit 8 and filter paper 9 have fully absorbed sufficient liquid. Excess test liquid is absorbed with an absorbent material. The glass frit 10 is placed centrally upon the filter paper 9. Care should be taken that the glass frit 10 is likewise fully saturated with test liquid. 1.8 g±0.005 g of the absorbent material to be tested are now sprinkled evenly upon the sieve floor 3 of apparatus 1 and the sample is loaded with the weight 4. On a different balance (measurement accuracy 0.01 g) to balance 5, the weight of the apparatus is determined m1. The apparatus 1 is then placed in front of support 6 on balance 5. Balance 5 is tared.

The measurement is then started, in that apparatus 1 is placed upon glass frit 10 and distance ring 11, which is located upon the glass frit 8 which has filter paper 9 laid upon it and which is located in depression 7. After placing apparatus 1, the respective absorption of test liquid, $M_{abs\ 0s}$ to $M_{abs\ 3600s}$ by the absorbent material is shown in intervals of 10 seconds. This occurs by the use of a computer-supported display program (Weighing Inn 1.0, Herbert Werth 1999©; a "Visual Basic for Application" module for Microsoft® Excel© can also be used, for example). The measurement lasts for one hour. If the absorption curve resulting from the measurement does not attain the maximum possible absorption, characterized in that the change of the measurement value at the end of the measurement is >0.1 g/60 s, the apparatus is placed upon a glass frit which is the same as glass frit 8 and which lays in a petri dish with a minimum diameter of 150 mm filled to the upper edge of the glass frit with test liquid. The absorption of test liquid is checked at delays of 1 to 60 minutes until the absorption is <0.1 g/60 s. The apparatus 1 is then weighed on a balance (precision 0.01 g) different to balance 5 ($m_2$). The maximum absorption is calculated from:

$$\text{Abs.}_{max} = m_2 - m_1$$

By means of the weight measurement using balance 5, the absolute amount of test liquid absorption at the defined times are recorded. In an $\text{absorption}_{absolute}$/time diagram, the absorbed liquid amount $m_{absXs}$ at a given time are plotted against time t. In addition, an $\text{absorption}_{relative}$/time diagram is generated. To this end, each measurement value $m_{absXs}$ in percent, based upon $\text{Abs.}_{max}$, is plotted against time t.

$$m_{absXS}[\%] = (m_{absXs}[g] * 100) / \text{Abs.}_{max}[g]$$

It can then be read from the $\text{absorption}_{relative}$/time diagram whether and after what time 50% or 90% of the maximum absorption ($\text{Abs.}_{max}$) have been reached.

Determination of the Acquisition Time and Rewet

The determination of the acquisition time and of the rewet occurred according to the test procedures described in DE-A-10249822.

First an airlaid composite is produced based upon M & J Fibretch Technology. A pressed cellulose fiber (with mass per unit area $m_{(fluff\ pulp)}$ and width $b_{(fluff\ pulp)}$, manufacturer: Stora Enso, Finland; type: Store EF semi-treated) was fed into a hammer mill with speed $v_{(fluff\ pulp-hammer\ mill)}$ and defibrated. A blower draws off the fibers continuously. In the same air stream, a bicomponent fiber (producer: Danaklon, now Fiber Visions, Denmark; type: AL-Thermal-C phil 6 mm, 3.3 dtex, 40 raw white) is dosed. To this end, the amount $m_{(bicomponent\ fiber\ discharge)}$ is dosed into an automatic weighing device. This device discharges the bicomponent amount every 40 cm (length of the weighing device) onto a conveyer belt which runs continuously with speed $v_{(bicomponent\ fiber\ dosing)}$. The water-absorbing polymer structure is dosed with a gravimetric dosing screw with mass flow $m_{(water-absorbing\ polymer\ structure)}$ into an entry device (Venturi-system) and introduced into the air stream on the pressure side of the blower. The mixture fiber/water-absorbing polymer structure is continuously laid upon the conveyer belt, which is overlaid with a tissue (mass per unit area $m_{(tissue)}$; manufacturer: Finess Hygiene AB, Sweden; type: Art.-No. 50330, quality KB 1800 Diapor-Tissue-Open), with the airlaid installation (speed $v_{(air\ laid-conveyer\ belt)}$, width $b_{(air\ laid)}$). Before rolling up at the end of the conveyer belt, another tissue (mass per unit area $m_{(tissue)}$; manufacturer: Finess Hygiene AB, Sweden; type: Art.-No. 50330, quality KB 1800, Diapor-Tissue-Open) is laid upon the airlaid composite and then rolled onto a cardboard roll. The airlaid composite is then fixed thermally in a continuously operating circulating air dryer (parameters: speed of flow $v_{(dryer)}$, temperature $T_{(dryer)}$, air speed $v_{(dryer\ air)}$, dwell time $t_{(dryer)}$).

The individual parameters are summarized again in the following table:

| Parameter | Value | Unit |
|---|---|---|
| $b_{(fluff\ pulp)}$ | 140 | mm |
| $m_{(fluff\ pulp)}$ | 800 | g/m$^2$ |
| $v_{(fluff\ pulp-hammer\ mill)}$ | 3.4 | m/min |
| $v_{(air\ laid-conveyer\ belt)}$ | ≈3.2 | m/min |
| $b_{(air\ laid)}$ | ≈350 | mm |
| $v_{(bicomponent\ fiber\ dosing)}$* | ≈0.8 | m/min |
| $m_{(bicomponent\ fiber/discharge)}$ | 10 | g |
| $m_{(water-absorbing\ polymer\ structure)}$ | 380 | g/min |
| $m_{(tissue)}$ (top and bottom layer) | 18 each | g/m$^2$ |
| $v_{(dryer)}$ | ≈0.5 | m/min |
| $T_{(dryer)}$ | 165 | °C. |
| $v_{(dryer,\ air)}$ | 2.4 | m/min |
| $t_{(dryer)}$ | ≈4 | min |

*corresponds to 2 discharges per minute

EXAMPLES

Production of an Untreated Water-Absorbing Polymer

A monomer solution consisting of 1200 g acrylic acid, 932.56 g 50% sodium hydroxide solution, 1,732.92 g deionized water. 1.8996 g monoallylpolyethyleneglycol-750-monoacrylic acid ester, 0.6192 g polyethyleneglycol-300-diacrylate and 24 g polyethyleneglycol-750-methoxymonomethacrylic acid ester was flushed with nitrogen to remove dissolved oxygen and cooled to the start temperature of 4° C. After reaching the start temperature, the initiator solution (1.2 g sodium peroxodisulfate in 38.8 g H$_2$O, 0.028 g 35.5% hydrogen peroxide solution in 7.72 g H$_2$O and 0.06 g ascorbic in 19.94 g H$_2$O added. After the end temperature of about 103° C. was reached, the resulting gel was comminuted and dried at 150° C. for 120 minutes. The dried polymer was coarsely broken up, milled, and sieved to a powder with a particle size of 150 to 850 µm (=powder A). In this process, milling and sieving were carried out such that the obtained powder A was characterized by the following particle size distribution: particles between 150 and 300 µm: 10 to 20 wt. %; particles between 300 and 600 µm: 40 to 60 wt. %; particles between 600 and 850 µm: 15 to 40 wt. %.

Powder A has a retention of 45 g/g and a SFC value of 0 s×cm$^3$/g.

Surface Post-crosslinking 100 g of powder A was coated with a solution of 1 g ethylene carbonate and 2.5 g water and heated for 40 minutes at 170° C. to carry out post-crosslinking. A powder B was obtained. This product showed 50% of the maximum Absorption under a Pressure of 20 g/cm$^2$ after about 42 minutes and 90% of the maximum Absorption under a Pressure of 20 g/cm$^2$ after more than one hour.

Example 1

Inventive 100 g of powder A was coated with a solution of 1 g ethylene carbonate, 2.5 g water and 0.75 g Al$_2$(SO$_4$)$_3$ and heated for 40 minutes at 170° C. to carry out the post-crosslinking. A powder C was obtained. This product showed 50% of the maximum Absorption under a Pressure of 20 g/cm$^2$ after about 10 minutes and 90% of the maximum Absorption under a Pressure of 20 g/cm$^2$ after about 23 minutes.

Example 2

Inventive 100 g of powder A was coated with a solution of 1 g ethylene carbonate, 2.5 g water and 1 g ZP30 (silica sol Levasil® 200/30 of the company Bayer) 0.75 g Al$_2$(SO$_4$)$_3$ and heated for 40 minutes at 170° C. to carry out the post-crosslinking. A powder D was obtained. This product showed 50% of the maximum Absorption under a Pressure of 20 g/cm$^2$ after about 13 minutes and 90% of the maximum Absorption under a Pressure of 20 g/cm$^2$ after about 27 minutes.

The water-absorbing polymer powders A to D are characterized by the following absorption properties:

| Powder | Retention [g/g] | AUL 0.7 psi [g/g] | SFC [10$^{-7}$ s × cm$^3$/g] |
|---|---|---|---|
| A | 45.0 | Not determined | 0 |
| B | 38.8 | 16.5 | 0 |
| C | 37.2 | 15.0 | 0 |
| D | 33.3 | 19.5 | 0 |

Example 3

Inventive 100 g of powder A were pre-warmed to 130° C. in the drying cupboard.

A mixture of 24 g Al$_2$(SO$_4$)$_3$×14H$_2$O, which had been milled in a centrifugal mill and sieved to a particle size within a range from 300 to 400 µm, 30 g Nanox® 200 (zinc oxide powder from the company Elementis Specialties, USA, with a BET surface area of 17 m$^2$/g and an average particle size of 60 nm), and 3.6 g polyethylene glycol 10,000 (polyethylene glycol with a molecular weight of 10,000 g/mol), which had likewise been milled in a centrifugal mill and sieved to a particle size of less than 300 µm, was prepared. 1.15 g of this mixture was combined in a Krups mixer by stirring with the pre-heated water-absorbing polymer structure.

Example 4

Using powders B, C, and D airlaid composites consisting of 350 g/m² cellulose fiber (fluff), 18 g/m² of a bicomponent fiber, 350 g/m² of the water-absorbing polymer structures according to the invention and 36 g/m² tissue were prepared according to the details in connection with the test procedure with the determination of the acquisition time and of the rewet, and the acquisition time and the rewet determined. The following measurement values were obtained:

| Powder | 1st Acquisition Time [sec] | 2nd Acquisition Time [sec] | 3rd Acquisition Time [sec] | Rewet [g] |
| --- | --- | --- | --- | --- |
| B | 38 | 806 | 2.477 | 3.2 |
| C | 22 | 378 | 1.472 | 2.6 |
| D | 24 | 307 | 1.053 | 2.6 |

It can be seen that the powders C and D according to the invention, although they have no observable permeability, are very well capable of further distributing large amounts of liquids entering a composite (recognizable in the comparably small values for the acquisition time).

| LIST OF REFERENCE NUMERALS | |
| --- | --- |
| 1 | apparatus for determination of the absorption under pressure |
| 2 | Plexiglas cylinder |
| 3 | floor made of sieve fabric |
| 4 | weight |
| 5 | balance |
| 6 | support |
| 7 | depression |
| 8 | glass frit (diameter 70 mm) |
| 9 | filter paper |
| 10 | glass frit (diameter 20 mm) |
| 11 | distance ring |
| 12 | silicon tube |
| 13 | liquid reservoir with ascending pipe |
| 14 | valve |
| 15 | valve |

What is claimed is:

1. A water-absorbing polymer structure comprising:
    from about 0.001 wt % to about 10 wt % of a compound selected from a SiO compound or a trivalent cation or a combination of the SiO compound and trivalent cation;
    wherein said water-absorbing polymer structure has the following properties:
    a a retention determined according to the herein-described test method of at least 32 g/g; and
    b a Time-dependent Absorption Against a Pressure (TAAP at 0.3 psi) determined according to the test method described herein of 20 g/cm², (TAAP; Time-dependent Absorption Against Pressure at 0.3 psi) selected from the group consisting of:
        b1 50% of the maximum absorption of the polymer structure within about 20 minutes and
        b2 90% of the maximum absorption of the polymer structure within about 40 minutes.

2. A composite comprising a water-absorbing polymer structure, which was produced according to a process, comprising the process steps of:
    I providing an untreated water-absorbing polymer structure (Pu) with a retention determined according to the test method described herein of at least about 37.5 g/g; and
    II bringing into contact of this water-absorbing, untreated polymer structure (Pu) with a permeability-increasing agent or a water-absorbing polymer structure according to claim 1, a substrate and if necessary an additive, wherein the composite comprises at least one region which comprises the water-absorbing polymer structure in an amount from about 30 to about 100 wt. %, based on the total weight of the relevant regions;
    wherein said permeability-increasing agent comprises from about 0.001 wt % to about 10 wt % of a compound selected from a SiO compound or a trivalent cation or a combination of the SiO compound and trivalent cation.

3. The composite according to claim 2, wherein the composite is an absorbent layer.

4. The composite according to claim 3, having at least one of the properties:
    (δ1) a Rewet value of at most about 3 g after the third wetting;
    (δ2) an Acquisition Time after the second wetting of at most about 450 s;
    (δ3) an Acquisition Time after the third wetting of at most about 1500 s.

5. The composite according to claim 2, wherein the composite has a mass per unit area of at least about 0.02 g/cm².

6. The composite according to claim 2, wherein the composite has a thickness of maximum about 20 mm.

7. A process for the production of a composite according to claim 2, wherein the water-absorbing polymer structure and the substrate, and optionally the additive are brought into contact with each other.

8. A water-absorbing polymer comprising,
    a) an untreated water-absorbing polymer structure (Pu) having a retention determined according to the test method "Determination of the Retention" described herein from about 40 to about 50 g/g; and
    b) a permeability-increasing agent located on the surface of the untreated water-absorbing polymer structure
    wherein the water-absorbing polymer further comprises from about 0.001 wt % to about 10 wt % of a compound selected from a SiO compound or a trivalent cation or a combination of the SiO compound and trivalent cation,
    wherein the foregoing compound is immobilized on the surface of the water-absorbing polymer.

9. The water-absorbing polymer structure according to claim 8, having an Absorption against a Pressure of 0.7 psi (50 g/cm²) determined according to ERT 442.2-02 of at least about 10 g/g.

10. A process for the production of water-absorbing polymer structures, comprising the following steps:
    I providing an untreated water-absorbing polymer structure (Pu) having a retention determined according to the test method "Determination of the Retention" described herein from about 40 to about 50 g/g; and
    II bringing into contact of the water-absorbing, untreated polymer structure (Pu) with from about 0.00 wt % to about 10 wt % of a compound selected from a SiO compound or a trivalent cation or a combination of the SiO compound and trivalent cation;
    wherein said water-absorbing polymer structure has the following properties:
    a a retention determined according to the herein-described test method of at least 32 g/g; and b a Time-dependent Absorption Against a Pressure (TAAP at 0.3 psi) determined according to the test method described herein of 20 g/cm$^2$, (TAAP; Time-dependent Absorption Against Pressure at 0.3 psi) selected from the group consisting of:

b1 50% of the maximum absorption of the polymer structure within about 20 minutes and b2 90 % of the maximum absorption of the polymer structure within about 40 minutes.

11. The process according to claim 1, wherein the SiO compound which was obtained by polycondensation of monoorthosilicic acid.

12. The process according to claim 4, wherein the SiO compound is a silica sol.

13. The process according to claim 1, wherein the trivalent cation is an $Al^{3+}$ ion.

14. The process according to claim 6, wherein the salt is selected from $AlCl_3 \times 6\ H_2O$, $NaAl(SO_4)_2 \times 12\ H_2O$, $KAl(SO_4)_2 \times 12\ H_2O$ or $Al_2(SO_4)_3 \times 14\text{-}18\ H_2O$.

15. The process according to claim 1, wherein the water-absorbing polymer structures are post-crosslinked before, during or after process step II.

16. A water-absorbing polymer structure obtainable by a process according to claim 1.

* * * * *

UNITED STATES PATENT AND TRADEMARK OFFICE
CERTIFICATE OF CORRECTION

PATENT NO. : 8,071,202 B2
APPLICATION NO. : 11/912011
DATED : December 6, 2011
INVENTOR(S) : Franck Furno et al.

It is certified that error appears in the above-identified patent and that said Letters Patent is hereby corrected as shown below:

Title Page, correct the Inventors data in item (75) with the following paragraph:

-- Inventors: Franck Furno, Düsseldorf (DE); Harald Schmidt, Tonivorst (DE); Peter Herbe, Duisburg (DE); Ursula Nielinger, Krefeld (DE); Michael Keup, Essen (DE) --.

Column 24,
Line 13, "of the relevant regions;" should read -- of the relevant region; --.

Line 60, "with from about 0.00 wt %" should read -- with from about 0.001 wt % --.

Column 25,
Lines 11-12, Claim 11, "according to claim 1, wherein the SiO compound which was" should read -- according to claim 10, wherein the SiO compound is a compound which was --.

Column 26,
Line 1, Claim 12, "according to claim 4" should read -- according to claim 11 --.

Line 3, Claim 13, "according to claim 1" should read -- according to claim 10 --.

Line 5, Claim 14, "according to claim 6" should read -- according to claim 13 --.

Line 8, Claim 15, "according to claim 1" should read -- according to claim 10 --.

Line 12, Claim 16, "according to claim 1" should read -- according to claim 10 --.

Signed and Sealed this
First Day of May, 2012

David J. Kappos
*Director of the United States Patent and Trademark Office*